(12) United States Patent
Besson et al.

(10) Patent No.: US 9,579,075 B2
(45) Date of Patent: Feb. 28, 2017

(54) DETECTOR ARRAY COMPRISING ENERGY INTEGRATING AND PHOTON COUNTING CELLS

(71) Applicant: ANALOGIC CORPORATION, Peabody, MA (US)

(72) Inventors: Guy M. Besson, Peabody, MA (US); Charles Shaughnessy, Hamilton, MA (US); Douglas Abraham, Topsfield, MA (US)

(73) Assignee: Analogic Corporation, Peabody, MA (US)

( * ) Notice: Subject to any disclaimer, the term of this patent is extended or adjusted under 35 U.S.C. 154(b) by 67 days.

(21) Appl. No.: 14/433,148

(22) PCT Filed: Oct. 2, 2012

(86) PCT No.: PCT/US2012/058432
§ 371 (c)(1),
(2) Date: Apr. 2, 2015

(87) PCT Pub. No.: WO2014/055066
PCT Pub. Date: Apr. 10, 2014

(65) Prior Publication Data
US 2015/0223766 A1 Aug. 13, 2015

(51) Int. Cl.
*A61B 6/00* (2006.01)
*G01N 23/00* (2006.01)
(Continued)

(52) U.S. Cl.
CPC ............ *A61B 6/4241* (2013.01); *A61B 6/035* (2013.01); *A61B 6/482* (2013.01); *G01T 1/2985* (2013.01)

(58) Field of Classification Search
USPC .............. 250/339.02, 339.06, 358.1, 363.01, 250/370.08, 370.09, 370.1, 393, 39, 3.02,
(Continued)

(56) References Cited

U.S. PATENT DOCUMENTS

| | | | |
|---|---|---|---|
| 6,339,632 B1 * | 1/2002 | Besson | G06T 11/005 378/15 |
| 6,351,514 B1 * | 2/2002 | Besson | G01T 1/1644 378/15 |

(Continued)

FOREIGN PATENT DOCUMENTS

DE 102011076351 A1 8/2012

OTHER PUBLICATIONS

International Search Report cited in related application No. PCT/US12/058432 dated Aug. 9, 2013, pp. 12.

*Primary Examiner* — Bernard Souw
(74) *Attorney, Agent, or Firm* — Cooper Legal Group, LLC

(57) ABSTRACT

Among other things, one or more techniques and/or systems are described for measuring the attenuation of a line integral through an object via a photon counting cell (302) and via an energy integrating cell (304). That is, an imaging apparatus is provided that comprises a radiation source (208) and a detector array (210). The detector array is comprised of both photon counting cells (302) and energy integrating cells (304) arranged such that, during an examination of the object, attenuation of a line integral through the object is measured by at least one photon counting cell and at least one energy integrating cell. In this way, at least two substantially complete views of an object may be acquired, one from measurements yielded from the photon counting cell (Continued)

(and other photon counting cells) and one from measurements yielded from the energy integrating cell (and other energy integrating cells).

20 Claims, 5 Drawing Sheets

(51) Int. Cl.
 *G01T 1/29* (2006.01)
 *A61B 6/03* (2006.01)
(58) Field of Classification Search
 USPC ................................ 250/526; 378/4, 19, 210
 See application file for complete search history.

(56) References Cited

U.S. PATENT DOCUMENTS

| | | | |
|---|---|---|---|
| 6,459,754 B1* | 10/2002 | Besson | A61B 6/032 378/15 |
| 7,433,443 B1* | 10/2008 | Tkaczyk | A61B 6/032 378/19 |
| 7,916,831 B2* | 3/2011 | Sun | A61B 6/032 250/370.09 |
| 8,781,062 B2* | 7/2014 | Besson | G01N 23/04 378/16 |
| 9,057,788 B2* | 6/2015 | Abraham | G01T 1/1647 |
| 2007/0147574 A1* | 6/2007 | Bernard De Man | A61B 6/032 378/4 |
| 2009/0274266 A1* | 11/2009 | Sun | A61B 6/032 378/19 |
| 2011/0211667 A1* | 9/2011 | Ikhlef | A61B 6/032 378/19 |
| 2013/0200269 A1* | 8/2013 | Abraham | G01T 1/1647 250/393 |
| 2013/0259202 A1* | 10/2013 | Sloutsky | H04B 5/0093 378/98 |
| 2013/0343515 A1* | 12/2013 | Besson | G01N 23/04 378/16 |
| 2015/0356755 A1* | 12/2015 | Shen | G01T 1/2985 378/19 |

\* cited by examiner

DETECTOR ARRAY COMPRISING ENERGY INTEGRATING AND PHOTON COUNTING CELLS

BACKGROUND

The present application relates to the field of imaging apparatuses. It finds particular application to imaging apparatuses that employ radiation (e.g., x-rays, gamma-rays, etc.) to image an object. For example, medical, security, and/or industrial applications may utilize a computed tomography (CT) apparatus to examine an object. Based upon the attenuation experienced by radiation traversing the object, one or more images of the object may be generated from the examination.

Today, CT and other imaging apparatuses that employ radiation technology (e.g., single-photon emission computed tomography (SPECT), mammography, digital radiography, etc.) are useful to provide information, or images, of interior aspects of an object under examination. Generally, the object is exposed to radiation comprising photons (e.g., such as x-rays, gamma rays, etc.), and an image(s) is formed based upon the radiation absorbed and/or attenuated by the interior aspects of the object, or rather an amount of photons that is able to pass through the object. Generally, highly dense aspects of the object absorb and/or attenuate more radiation than less dense aspects, and thus an aspect having a higher density, such as a bone or metal, for example, will be apparent when surrounded by less dense aspects, such as muscle or clothing.

Imaging apparatuses that employ radiation technology generally comprise, among other things, a detector array having of a plurality of cells respectively configured to convert radiation that has traversed the object into signals that may be processed to produce the image(s). The cells are typically "energy integrating" or "photon counting" type cells (e.g., the imaging apparatus operates in energy integrating mode or photon counting mode).

Energy integrating cells are configured to convert energy into signals (e.g., current or voltage signals) that are proportional to an incoming photon flux rate and a photon energy. That is, charge collected in respective cells is integrated over a time period (e.g., at times referred to as a measurement interval), sampled, and digitized. While this type of cell is widely used, there are several drawbacks to energy integrating cells. For example, energy integrating cells are generally not able to provide feedback as to the number and/or energy of photons detected. As another drawback, there is a lower limit of detection defined by noise such that a cell with little to no incident radiation may produce some signal due to thermal and/or analog read noise (e.g., produced by the detector array and/or readout components). It may be appreciated that as a result of this lower limit, the dose of radiation that is applied to an object under examination is generally greater than the dose of radiation that may be applied to the object if the cells are of a photon counting type.

Photon counting cells are configured to output signals for respective detection events and may be configured to convert energy into signals that are proportional to the energy of a detected photon (e.g., at times referred to as a detection event). Thus, ideally, signals produced by respective cells generally comprise one or more current and/or voltage pulses, for example, respectively associated with a single detection event. By way of example, in one embodiment an output signal is proportional to the energy of a detected photon and in anther embodiment an output signal merely corresponds to a photon count. A controller may then be used to determine the location and energy of respective detection events, accumulate the detection events occurring during a measurement interval (e.g., an "acquisition view"), digitize the information, and/or process the digital information to form an image, for example. It may be appreciated that there are numerous advantages to photon counting cells over energy integrating cells. For example, the counting of photons is essentially noise free (e.g., apart from inherent photon shot noise). Therefore, a lower dose of radiation may be applied to the object under examination. Moreover, photon counting cells generally allow for energy or wavelength discrimination. Therefore, images resulting from radiation emitted at different energy levels may be obtained at the same or substantially the same time, for example.

While photon counting detector arrays (e.g., detector arrays comprising photon counting cells) have numerous advantages over energy integrating detector arrays, photon counting detector arrays have not been widely applied in some imaging modalities (e.g., such as in CT apparatuses) due to cost considerations and other challenges associated with photon counting detector arrays. For example, CT systems generally have a high flux rate, which may cause saturation issues (e.g., pulse pileup) in photon counting detector arrays because photon counting cells may be unable to return to a normal state after the detection of a photon and before another photon is detected.

SUMMARY

Aspects of the present application address the above matters, and others. According to one aspect an imaging apparatus is provided. The apparatus comprises an examination region configured to selectively receive an object under examination and a radiation source. The apparatus also comprises a detector array configured to detect radiation emitted from the radiation source that has traversed the object. The detector array comprises energy integrating cells and photon counting cells.

According to another aspect, a method for imaging an object is provided. The method comprises performing a helical scan on an object using a radiation source and a detector array. For a first line integral through the object, the method comprises measuring attenuation of the first line integral via an energy integrating cell of the detector array and measuring the attenuation of the first line integral via a photon counting cell of the detector array.

According to yet another aspect a computed tomography apparatus for medical imaging is provided. The apparatus comprises an examination region configured to selectively receive an object under examination and a radiation source. The apparatus also comprises a detector array configured to detect radiation emitted from the radiation source that has traversed the object. The detector array has an arcuate detection surface. A first portion of the arcuate detection surface comprises photon counting cells and a second portion of the arcuate detection surface comprises energy integrating cells. The apparatus also comprises a rotating gantry configured to rotate the radiation source and the detector array about the examination region during a helical examination of the object.

Those of ordinary skill in the art will appreciate still other aspects of the present application upon reading and understanding the appended description.

FIGURES

The application is illustrated by way of example and not limitation in the figures of the accompanying drawings, in which like references generally indicate similar elements and in which.

DESCRIPTION

Figure 1:
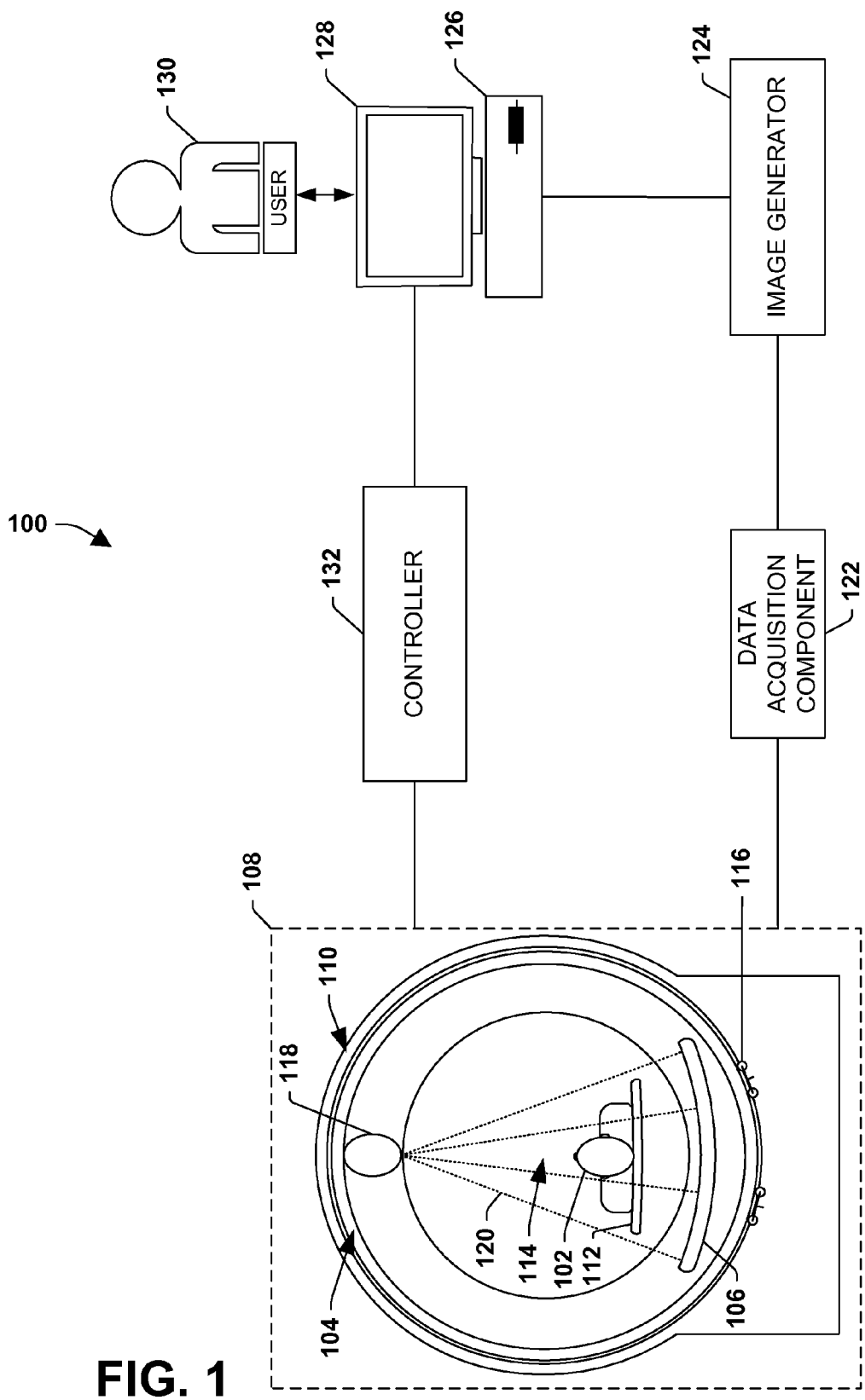
FIG. 1 illustrates an example environment of an imaging apparatus.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, one or more systems and/or techniques are provided herein for measuring attenuation of an object (e.g., or a line integral through the object) using an energy integrating cell and for measuring attenuation of the object (e.g., or the line integral through the object) using a photon counting cell. In this way, for a given line integral through the object, a measurement may be acquired from an energy integrating cell and a measurement may be acquired from a photon counting cell. In one embodiment, data yielded from these two measurements may be combined and utilized to generate an image of the object under examination. It may be appreciated that by having a photon counting measurement (e.g., a measurement acquired from the photon counting cell) and an energy integrating measurement (e.g., a measurement acquired from the energy integrating cell), information may be acquired that is unable to be acquired from either measurement individually. For example, pulse pileup, represented in the photon counting measurement, may be corrected using the energy integrating measurement. As another example, energy information may be derived from the energy integrating measurement using the photon counting measurement.

To acquire the photon counting measurement and the energy integrating measurement, a detector array of the imaging system comprises a set of one or more energy integrating cells and a set of one or more photon counting cells. Example arrangements of such detector cells may be described below. However, in one embodiment, such as in a CT system, the energy integrating cells and the photon counting cells may be arranged such that respective line integrals passing through the object may be measured by at least one energy integrating cell and at least one photon counting cell during a helical scan of the object. Thus, a first group of one or more rows of the detector array (e.g., where a row extends in the x-direction perpendicular to the axial direction) may comprise photon counting cells and a second group of one or more rows of the detector array may comprise energy integrating cells.

FIG. 1 is an illustration of an example environment 100 of an imaging modality that may be configured to generate data representative of an object 102 (e.g., a patient, baggage, etc.) or an aspect thereof under examination. More specifically, FIG. 1 illustrates an example environment 100 comprising an example CT apparatus configured to acquire volumetric data indicative of the object 102. In one embodiment, such volumetric data may be utilized to reconstruct two-dimensional (2D), three-dimensional (3D), four-dimensional (4D), etc. images of the object 102.

It may be appreciated that while the example environment 100 describes a CT apparatus, other X-ray imaging apparatuses and/or other radiation imaging apparatus (e.g., such as imaging modalities that employ gamma radiation) are also contemplated. For example, scanning line systems and/or projection systems may be utilized to generate two-dimensional images of an object. Moreover, the arrangement of components and/or the types of components included in the example environment 100 are merely provided as examples. By way of example, in another embodiment, the data acquisition component 122 may be comprised within the detector array 106.

In the example environment 100, an examination unit 108 of the CT system is configured to examine one or more objects 102. The examination unit 108 can comprise a rotating gantry 104 and a (stationary) support structure 110 (e.g., which may encase and/or surround at least a portion of the rotating gantry 104 (e.g., as illustrated with an outer, stationary ring, surrounding an outside edge of an inner, rotating ring)). During an examination of the object(s) 102, the object(s) 102 can be placed on a support article 112, such as a bed or conveyor belt, for example, that is selectively positioned in an examination region 114 (e.g., a hollow bore in the rotating gantry 104) configured to selectively receive the object(s) 102, and the rotating gantry 104 can be rotated and/or supported about the object(s) 102 by a rotator 116, such as a motor, drive shaft, chain, roller truck, etc.

The rotating gantry 104 may surround a portion of the examination region 114 and may comprise one or more radiation sources 118 (e.g., an ionizing radiation source such as an x-ray source) and a detector array 106 that is mounted on a substantially diametrically opposite side of the rotating gantry 104 relative to the radiation source(s) 118. In this way, the relative position of the radiation source(s) 118 and the detector array 106 (e.g., the position of the radiation source(s) 118 relative to the detector array 106) may be maintained during an examination of the object 102, for example.

During an examination of the object(s) 102, the radiation source(s) 118 emits fan, cone, wedge, and/or other shaped radiation 120 configurations from a focal spot(s) of the radiation source(s) 118 (e.g., a region within the X-ray source(s) 118 from which radiation 120 emanates) into the examination region 114. It may be appreciated that such radiation 120 may be emitted substantially continuously and/or may be emitted intermittently (e.g., a brief pulse of radiation is emitted followed by a resting period during which the radiation source(s) 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 can comprise a linear or two-dimensional array of cells disposed as a single row or multiple rows in the shape of a circular, cylindrical, or spherical arc, for example, typically having a center of curvature at the focal spot of the radiation source(s) 118, for example. As the rotating gantry 104 rotates, the detector array 106 is configured to convert detected radiation into analog signals. Alternatively, in other embodiments, such as in mammography systems, the detector array 106 may be a flat panel detector and the cells may be arranged in a plane.

As may be described in more detail below, the detector array is comprised of energy integrating cells configured to convert energy into signals (e.g., current or voltage signals) that are proportional to an incoming photon flux rate and energy of respective photons and photon counting cells configured to convert respective detection events into signals (e.g., which may be proportional to the energy of a detected photon). That is, the energy integrating cells are configured to read-out the charge that has accumulated at the cell during a specified period of time (e.g., due to a plurality of detection events) (e.g., where the charge generated for each photon detection event is typically proportional to the photon energy), whereas the photon counting cells are typically configured to read-out charge for respective detection events.

Signals that are produced by the detector array 106 or rather by the cells of the detector array 106 may be transmitted to a data acquisition component 122 that is in operable communication with the detector array 106 and configured to process the signals using pertinent signal processing techniques. In one embodiment, signals produced by the energy integrating cells may be processed differently than signals produced by the photon counting cells. The output of the data acquisition component 122 may be referred to as projection data or measurement data and may be indicative of the attenuation of radiation measured by respective cells of the detector array 106. Moreover, measurement data yielded from respective energy integrating cells during a view (e.g., a specified period of time) may be combined and/or measurement data yielded from respective photon counting cells during a view may be combined. In this way, measurement data acquired while the radiation source(s) 118 and the detector array 106 were at a particular angular range relative to the object 102 may be combined to form a projection for that particular angular range, for example.

The example environment 100 further comprises an image generator 124 configured to receive the projection data that is output by the data acquisition component 122.

The image generator 124 is configured to generate image data (also referred to as image(s)) from the projection data using a suitable analytical, iterative, and/or other reconstruction technique (e.g., filtered-backprojection reconstruction, tomosynthesis reconstruction, iterative reconstruction, etc.). In this way, the data is converted from projection space to image space, a domain that may be more understandable by a user 130 viewing the image(s), for example.

The example environment 100 further comprises a terminal 126, or workstation (e.g., a computer), that may be configured to receive the image data (e.g., output by the image generator 124). The terminal 126 may also be configured to present the image data for display on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the object examination unit 108 (e.g., a speed to rotate, a speed and direction of a conveyor belt, etc.), for example.

In the example environment 100, a controller 132 is operably coupled to the terminal 126. The controller 132 may be configured to control operations of the examination unit 108, the data acquisition component 122, and/or the image generator 124, for example. By way of example, in one embodiment, the controller 132 may be configured to receive information from the terminal 126 and to issue instructions to the examination unit 108, the data acquisition component 122, and/or the image generator 124 indicative of the request. For example, the controller 132 may provide instructions for maneuvering the support article 112 and/or turning on/off the examination unit 108.

It may be appreciated that the example component diagram is merely intended to illustrate one embodiment of one type of imaging modality and is not intended to be interpreted in a limiting manner. For example, the functions of one or more components described herein may be separated into a plurality of components and/or the functions of two or more components described herein may be consolidated into merely a single component. Moreover, the imaging modality may comprise additional components configured to perform additional features, functions, etc. and/or some components described herein may be optional.

Figure 2:
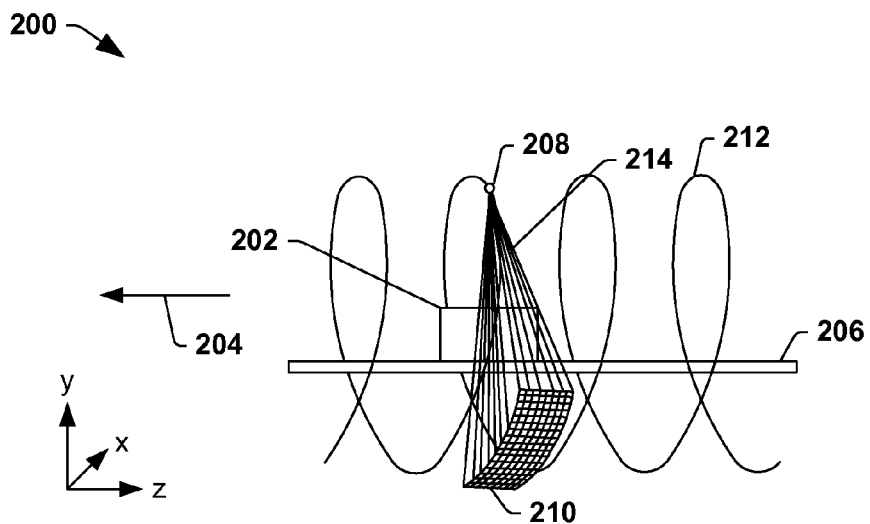
FIG. 2 illustrates a functional diagram of a helical scan performed via a CT imaging modality.

FIG. 2 is a functional diagram 200 of a helical scan performed via a CT imaging modality, such as in security and/or medical applications. In such an imaging modality, an object 202 (e.g., 102 in FIG. 1) under examination is translated 204 (e.g., at a constant speed, in a step-and shoot manner, etc.) in an axial direction (e.g., parallel to an axis of rotation) via an object support 206 (e.g., 112 in FIG. 1) during the examination of the object 202. That is, the object 202, for example, may be translated at a constant speed (e.g. to form a traditional helical loop) or may be moved in a step-and-shoot manner, where the object is translated between rotations or rotation segments. It may be appreciated that as used herein, helical scan, helical scanning, and/or the like is intended to be used to describe both translation at a constant speed and periodic translation (e.g., such as performed with respect to step-and-shoot).

While the object is being translated and/or between translations, the object 202 is exposed to radiation 214. That is, one or more radiation sources 208 (e.g., 118 in FIG. 1) are configured to emit radiation 214, causing the object 202 to be exposed to radiation 214. A detector array 210 (e.g., 106 in FIG. 1), mounted on a substantially diametrically opposite side of the object 202 relative to the radiation source(s) 208, is configured to detect radiation 214 that has traversed the object 202. In this way, by emitting and detecting radiation 214, the object 202 is examined.

In a CT imaging modality, the radiation source(s) 208 and the detector array 210 are typically rotated about the object 202 (e.g., in an x-y plane) via a rotating gantry (e.g., 104 in FIG. 1) during the examination. Thus, in an environment where the object 202 is translated at a substantially constant speed, such a rotation may cause the radiation source(s) 208 and/or the detector array 210 to follow a spiral or helical-like trajectory 212 relative to the object (e.g., where the radiation source(s) 208 and detector array 210 do not move in the axial direction, and thus the helical trajectory is established by the combination of the xy rotation of the radiation source 208 and detector array 210 and the axial direction translation 204 of the object 202).

It may be appreciated that for purposes of the instant application, the axial direction (e.g., the z-direction) may be defined as a direction parallel to the axis of rotation. Typically, the object 202 is translated along the axial direction. The detector array 210 may be said to have a z-direction and an x-direction (e.g., although it may have some y-component due to the arcuate shape of the detector array 210). Thus, the x-direction may be a direction of the detector array 210 that is perpendicular to the z-direction. The y-direction may be defined as the dimension extending between the radiation source 208 and the detector array 210. It may be appreciated that relative orientations may change as elements rotate and/or move. For example, the y-direction may be perpendicular to the z-direction at 0 and 180 degrees of rotation, but may be parallel to the z-direction at 90 and 270 degrees of rotation.

Figure 3:
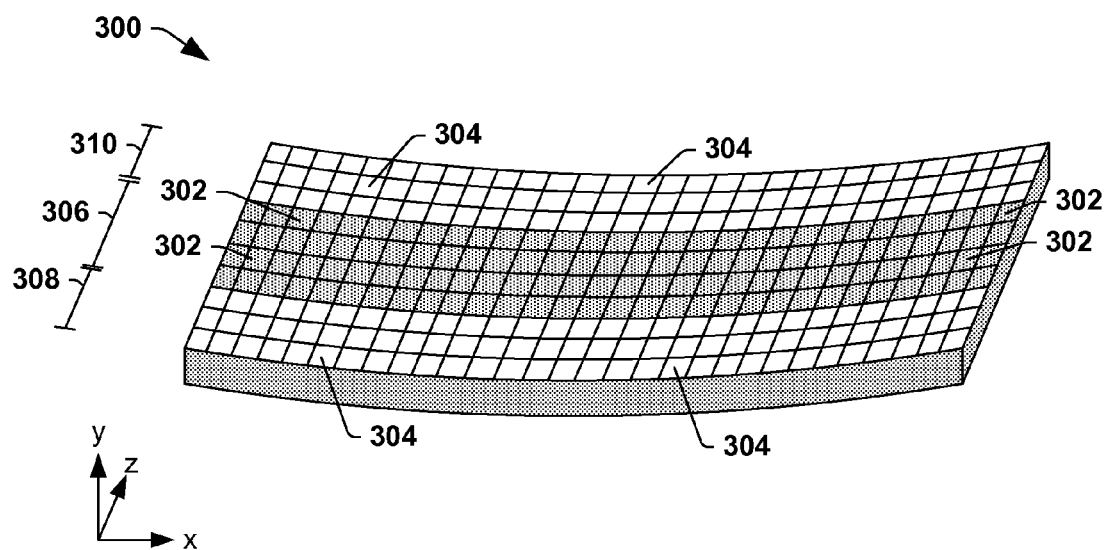
FIG. 3 illustrates an example arrangement of photon counting cells and energy integrating cells in an example detector array.
Figure 4:
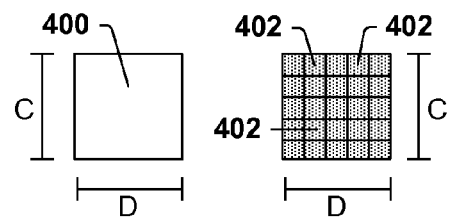
FIG. 4 illustrates a relative size of a surface area of an energy integrating cell in relation to a surface area of a photon counting cell.
Figure 5:
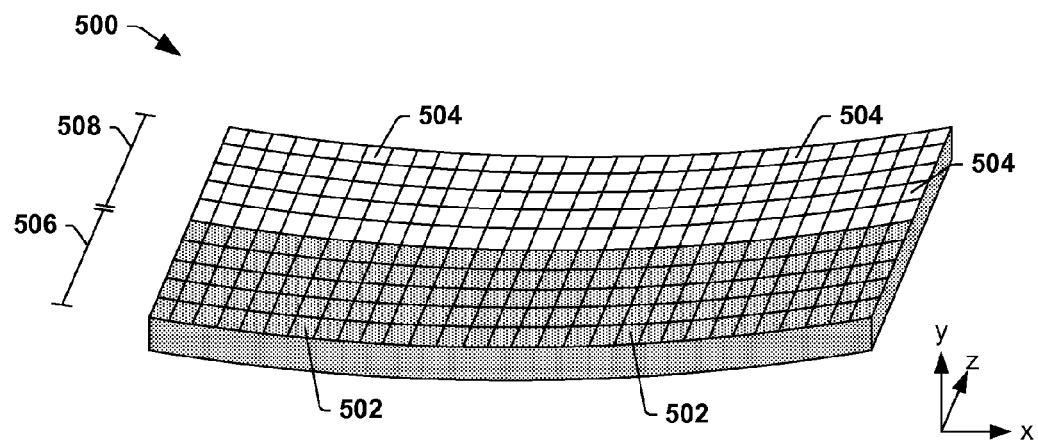
FIG. 5 illustrates an example arrangement of photon counting cells and energy integrating cells in an example detector array.

As may be illustrated in FIGS. 3-5, the detector array 210 is comprised of photon counting cells and energy integrating cells, which may be generically referred to herein as cells. That is, when reference is being made to both photon counting cells and energy integrating cells, the generic term cell or cells may be utilized. For example, the detector array 210 is generically comprised of cells (e.g., also referred to as detector cells), a portion of those cells may be photon counting cells (e.g., cells configured to operate in photon counting mode) and a portion of those cells may be energy integrating cells (e.g., cells configured to operate in energy integrating mode).

The photon counting cells and the energy integrating cells are typically arranged such that respective line integrals through an object being examined (or intending to be examined by the system) are measured by at least one energy integrating cell and at least one photon counting cell. That is, the photon counting cells and the energy integrating cells are arranged such that, during a helical scan, a line integral passing through the object 202 is measured at least twice. At least one measurement of the line integral is obtained by a photon counting cell (e.g., which may be referred to herein as a photon counting measurement) and at least one measurement of the line integral is obtained by an energy integrating cell (e.g., which may be referred to herein as an energy integrating measurement). As an example, a line integral may be measured by a first energy integrating cell (e.g., based upon attenuation of radiation following a path of the line integral) during a first rotation segment (e.g., a first full rotation, half-rotation, etc.) of a helical scan and may be measured by a first photon counting cell during a second rotation segment (e.g., a second full rotation, second half rotation, etc.), which may be different than the first rotation segment.

It may also be appreciated that it may be difficult to measure the same line integral using both a photon counting cell and an energy integrating cell due to the geometry of the detector array 210 and/or the placement of photon counting cells and energy integrating cells within the detector array 210. Thus, the measurement of the line integral obtained by the first energy integrating cell may be a measurement of a slightly different line integral than the measurement obtained by the first photon counting cell, for example. In one embodiment, slight differences in the line integral (e.g., due to the geometry of the detector array) may be corrected during image generation/reconstruction, for example. Thus, while reference may be made to measuring the same line interval via an energy integrating cell and a photon counting cell, the line integral measured by an energy integrating cell may be slightly different than the line integral measured by a photon counting cell due to geometric differences of the cells inherent in the detector array, for example. However, such differences may be addressed during image generation and/or reconstruction such that that the same line interval may be regarded as being measured by an energy integrating cell and a photon counting cell.

Moreover, it may be appreciated that while continued reference is made to measuring a line integral with a photon counting cell and with an energy integrating cell, a line integral may be measured by more than one photon counting cell and/or more than one energy integrating cell. Further, the number of photon counting cells that measure a line integral may be different than the number of energy integrating cells that measure the line integral. For example, a line integral may be measured by two energy integrating cells during a helical scan and may be measured by merely one photon counting cell.

The energy integrating cells and the photon counting cells may be constructed of materials known to those skilled in the art and may be configured for indirect conversation of radiation and/or direct conversation of radiation. By way of example, in one embodiment, the energy integrating cells may be of an indirect conversion type and the photon counting cells may be of a direct conversion type. As an example, the energy integrating cells may be comprised of a scintillator material configured to convert radiation impinging thereon into light energy and a photodetector configured to detect/measure the light energy and generate an electrical response (e.g., causing radiation to be indirectly converted into electrical energy). The photon counting cells may be comprised of a direct conversion material, such as cadmium zinc telluride (CZT), for example, configured for the direct conversion of radiation impinging thereon into electrical energy. In another embodiment, the energy integrating cells and the photon counting cells may both be of a direct conversion type or may both be of an indirect conversion type, for example.

FIG. 3 illustrates an example arrangement of photon counting cells 302 (e.g., represented by the shaded/dotted pattern) and energy integrating cells 304 (e.g., represented as not being patterned/shaded) in an arcuate detector array 300 (e.g., 210 in FIG. 2). As illustrated, the cells 302, 304 are arranged in a grid-like pattern comprised of columns and rows. As used herein, a row may refer to a set of cells 302, 304 extending in the x-direction and a column may refer to a set of cells 302, 304 extending in the z-direction. Thus, the example detector array 300 comprises 10 rows of cells 302, 304 and comprises 30 columns of cells 302, 304. Typically, a detector array for a CT system comprises more columns of cells than rows of cells, although in some embodiments the detector array 300 may comprise more rows than columns or an equal number of rows and columns.

Figure 6:
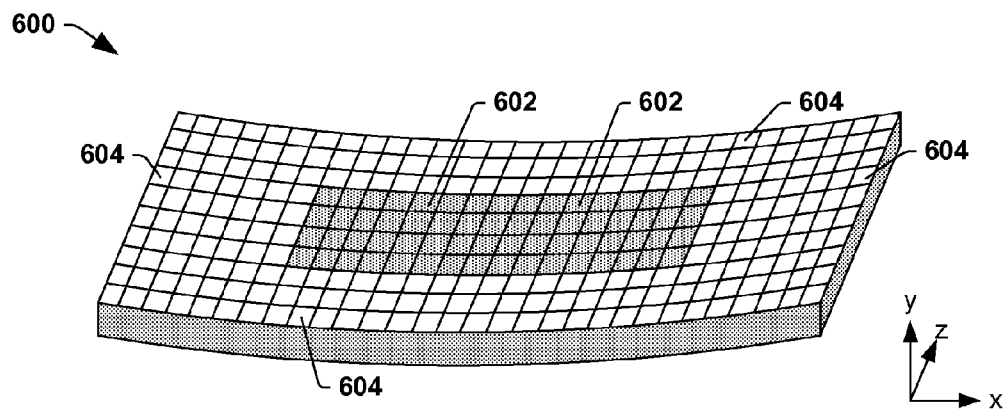
FIG. 6 illustrates an example arrangement of photon counting cells and energy integrating cells in an example detector array.

In this arrangement of cells 302, 304, respective rows are comprised of merely (e.g., exactly) one type of cell. For example, rows comprising photon counting cells 302 do not comprise energy integrating cells 304 and rows comprising energy integrating cells 304 do not comprise photon counting cells. In other arrangements, such as illustrated in FIG. 6, one or more rows may comprise both photon counting cells 302 and energy integrating cells 304. Further, in this particular arrangement, respective columns comprise both energy integrating cells 304 and photon counting cells 302.

In the example detector array 300, the rows of cells comprising photon counting detector cells 302 are neighboring rows (e.g., adjoining rows) and the rows of cells comprising energy integrating cells 304 are positioned in sets, where a first set is diametrically opposite a second set relative to the rows of cells comprising photon counting detector cells 302 (e.g., such that the first set is arranged on an opposite side of a detection surface of the detector array 300 relative to the second set and is separated from the second set by the photon counting detector cells 302). Thus, the example arrangement may be described as having a central portion 306 and edge portions 308, 310. The central portion 306 may be defined as one or more rows near a center of the detector array 300 and the edge portions 308, 310 may be defined as rows proximate edges of the detector array 300 (e.g., where the edges extend in the x-direction). In the illustrated embodiment, the center portion 306 comprises rows of photon counting cells 302 and the edge portions 308, 310 comprise rows of energy integrating cells 304.

In the example detector array 300, respective cells 302, 304 have approximately a same detection surface area (e.g., respective cells occupy approximately a same amount of surface area on the detector array 300). As such, the rows and columns are approximately uniformly sized. In another embodiment, some cells 302, 304 may occupy a different amount of surface area than other cells 302, 304. As an example, one or more energy integrating cells 304 may have a first detection surface area and one or more photon counting cells 302 may have a second detection surface area, which is different than the first detection surface area.

FIG. 4 provides a side-by-side example illustrating an energy integrating cell 400 (e.g., 304 in FIG. 3) that occupies a same amount of detection surface (e.g., labeled "C"×"D") as a group of photon counting cells 402 (e.g., 302 in FIG. 3). By way of example, the energy integrating cell 400 may measure 1 millimeter squared (e.g., "C" and "D" may respectively equal 1 millimeter). Thus, an energy integrating cell 400 may occupy approximately 1 millimeter squared of the detection surface. In the same amount of area, another portion of the detector array may be occupied by approximately 25 photon counting cells 402 (e.g., respectively measuring 0.04 millimeters squared). In this way, for every row and/or column of energy integrating cells, there may be five rows and/or five columns of photon counting cells, for example.

The size of energy integrating cells, the size of photon counting cells, and/or the relative size of the energy integrating cells and photon counting cells may depend upon, among other things, the flux rate of the radiation source (e.g., the amount of radiation photons emitted per unit time). For example, at higher flux rates, it may be desirable to reduce the detection surface area of respective photon counting cells to reduce the probability of pulse pileup in the photon counting cells (e.g., where energy integrating cells may be relatively unaffected by the higher flux rates). Conversely, where flux rates are low, the detection surface area of respective photon counting cells may be larger.

FIG. 5 illustrates another example arrangement of photon counting cells 502 (e.g., represented by the shaded/dotted pattern) and energy integrating cells 504 (e.g., represented as not being patterned/shaded) in an arcuate detector array 500 (e.g., 210 in FIG. 2). As illustrated, the cells 502, 504 are arranged in a grid-like pattern comprised of columns and rows. Respective rows are comprised of merely (e.g., exactly) one type of cell. For example, rows comprising photon counting cells 502 do not comprise energy integrating cells 504 and rows comprising energy integrating cells 504 do not comprise photon counting cells 502, although one or more rows having one or more energy integrating cells and one or more photon counting cells are contemplated. Respective columns are comprised of photon counting cells 502 and energy integrating cells 504, although one or more columns having merely energy integrating cells or merely photon counting cells are contemplated.

In the illustrated embodiment, the detector array 500 may be divided into two sides 506, 508 (e.g., with an imaginary line extending in the x-direction delineating the first side 506 from the second side 508). The first side 506 may comprise one or more rows of photon counting cells 502 and the second side 508 may comprise one or more rows of energy integrating cells 504. In the illustrated embodiment, the two sides 506, 508 are equal in length and the first side 506 comprises a same number of rows as the second side 508). However, in other embodiments, the two sides 506, 508 may be unequal in length and/or the number of rows in the first side 506 may not equal the number of rows in the second side 508. For example, as described with respect to FIG. 4, the detection surface area of respective energy integrating cells may be different (e.g., larger) than the detection surface area of respective photon counting cells. Thus, there may be more rows of photon counting cells 502 than there are energy integrating cells 504 in a detector array 500 having a detection surface (e.g., surface facing the radiation source) that is divided into halves, with a first half comprising photon counting cells 502 and a second half comprising energy integrating cells 504. In another embodiment, the amount of detection surface occupied by the energy integrating cells 504 may be different than an amount of detection surface occupied by the photon counting cells 502.

FIG. 6 illustrates yet another example arrangement of photon counting cells 602 (e.g., represented by the shaded/dotted pattern) and energy integrating cells 604 (e.g., represented as not being patterned/shaded) in an arcuate detector array 600 (e.g., 210 in FIG. 2). As illustrated, the cells 602, 604 are arranged in a grid-like pattern comprised of columns and rows. In this embodiment, at least some of the rows are comprised of both photon counting cells 602 and energy integrating cells 604. Further, at least some of the columns comprise merely energy integrating cells 604 (e.g., whereas no columns of the arrangements illustrated in FIGS. 3 and 4 comprised merely photon counting cells and/or merely energy integrating cells). Nevertheless, it will be appreciated that one or more rows and/or one or more columns having one or more energy integrating cells and one or more photon counting cells are contemplated. Similarly, one or more rows and/or one or more columns having merely energy integrating cells or merely photon counting cells are contemplated. Also, one or more rows and/or one or more columns having no energy integrating cells or no photon counting cells are contemplated.

In the example arrangement of FIG. 6, the photon counting cells 602 are arranged toward a center of the detector array 600 (e.g., where image reconstruction spatial sensitivity to artifacts, non-linearities, and inconsistencies might be higher and thus benefit more from photon counting cells 602). Rows and columns neighboring an edge (e.g., extending in the x-direction and/or z-direction) of the detector array 600 may thus be comprised of merely energy integrating cells 604 because the spatial sensitivity at edges of the detector array 600 is typically less than the spatial sensitivity near a center of the detector array 600. In this way, the photon counting cells 602 are arranged in a cluster and energy integrating cells 604 surround the cluster on one or more sides (e.g., forming an island of photon counting cells 602 near a center of the detector array 600).

In may be appreciated that the foregoing arrangements are merely example arrangements and are not intended to limit the scope of the instant disclosure, including the scope of the claims. For example, among other things, the number of rows and/or columns, the arrangement of the rows and/or columns (e.g., including the type(s) of cells comprised in respective rows and/or columns), the number of photon counting cells relative to the number of photon counting cells in the detector array, the total amount of detection surface occupied by the photon counting cells relative to the total amount of detection surface occupied by the energy integrating cells, the amount of detection surface occupied by a single photon counting cell relative to the amount of detection surface occupied by a single energy integrating cell, etc. may vary from the foregoing arrangements. For example, in an embodiment, respective rows and/or columns of the detector array may be comprised of both photon counting and energy integrating cells.

Moreover, the size of the detector array and/or the arrangement of photon counting cells and/or energy integrating cells within the detector array may be a function of, among other things, a desired/practical pitch (e.g., translation speed of the object in the z-direction) and/or a desired/practical rotational speed of the rotating gantry (e.g., in applicable). Thus, the cells may be arranged according to the pitch and/or rotational speed of the system to promote measuring respective line integrals through the object via at least one photon counting cell and at least one energy integrating cell. As such, in one embodiment, the cells may be arranged in any desired manner that achieves the result of acquiring a photon counting measurement (e.g., from a photon counting cell) and an energy integrating measurement (e.g., from an energy integrating cell) respectively indicating an amount of attenuation through a same (e.g., or substantially similar) line integral of the object. Moreover, it may be appreciated that in another embodiment, the cells may be arranged in a desired arrangement and the pitch and/or rotational speed may be a function of the desired arrangement (e.g., such that the pitch and/or rotational speed are a function of the arrangement of photon counting cells and energy integrating cells as opposed to the arrangement of cells being a function of a desired pitch and/or rotational speed).

In medical systems, where a living object is exposed to ionizing radiation, it may be desirable to reduce radiation exposure where possible (e.g., without substantially compromising the quality and/or usefulness of an image resulting from the examination). As such, in one embodiment, a pre-object filter (e.g., a pre-patient filter) may be devised to filter at least a portion of the radiation prior to exposing the object to the same. For example, a conventional bow-tie filter comprised of a suitable radiation attenuating material, such as Teflon, graphite, copper, aluminum, and/or other material(s) partially opaque to radiation, for example, may be utilized to filter a portion of the radiation prior to interaction with the object. Conventionally, such pre-object filters have been configured to attenuated radiation in the fan beam direction (e.g., in the x-direction within which the fan beam flares or widens out). As such, radiation directed towards one or more columns of detector cells may be attenuated differently than radiation directed toward one or more other columns of detector cells. In this way, radiation directed towards distal columns of cells may be attenuated more than radiation directed towards central columns of cells, for example, because measurements from distal columns are typically less significant to image reconstruction and image quality than more central columns, for example.

As provided for herein, a system may comprise a pre-object filter configured to filter radiation directed towards photon counting cells differently than radiation directed towards energy integrating cells. Such a pre-object filter may be configured to attenuate radiation in the fan-beam direction, in a cone beam direction (e.g., z-direction), and/or both. In this way, radiation directed towards photon counting cells (e.g., which are typically more sensitive to radiation flux and perform better at lower flux rates) may be attenuated differently than radiation directed towards energy integrating cells (e.g., which are typically less sensitive to radiation flux and perform better at high flux rates). For example, the pre-object filter may be configured to attenuate radiation directed toward photon counting cells more than directed toward energy integrating cells. In one embodiment, such differences in attenuation may be achieved by the pre-object filter by varying a thickness of a material that the radiation passes through. In another embodiment, such differences in attenuation may be achieved by using various materials for the pre-object filter. For example, a portion of the pre-object filter through which radiation directed towards the photon counting cells traverses may comprise a more radiation opaque material than a portion of the pre-object filter through which radiation directed towards the energy integrating cells traverses.

Figure 7:
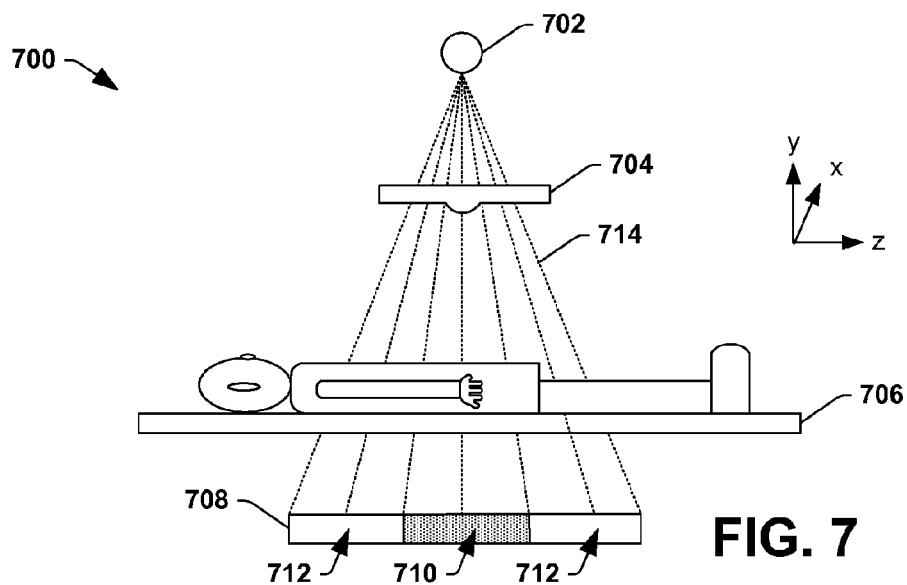
FIG. 7 illustrates a side-view of an example imaging apparatus comprising a pre-object filter.

FIG. 7 illustrates an example two-dimensional view (e.g., illustrating an Y-Z plane) of an example imaging apparatus 700 comprising a radiation source 702 (e.g., 118 in FIG. 1), a pre-object filter 704, a support article 706 (e.g., 112 in FIG. 1), and a detector array 708 (e.g., 106 in FIG. 1) comprising photon counting cells 710 (e.g., 302 in FIG. 3) and energy integrating cells 712 (e.g., 304 in FIG. 3). Such a pre-object filter 704 may be utilized, for example, in conjunction with a detector cell arrangement similar to the arrangement illustrated in FIG. 3, where the detector array 708 is comprised of a central portion of photon counting cells 710 and two edge portions of energy integrating cells 712. Where the arrangement of cells is different, the pre-object filter 704 may be shaped/configured differently to accommodate the different arrangement of cells.

In the example embodiment, the pre-object filter 704 is configured to attenuate radiation 714 directed toward the photon counting cells 710 differently than radiation 714 directed toward the energy integrating cells 712. In the illustrated embodiment, the thickness (e.g., measured in the y-direction) of the pre-object filter 704 is increased or made non-uniform over a portion of the pre-object filter along the z-axis such that radiation 714 directed towards the photon counting cells 710 is attenuated differently than radiation 714 directed towards the energy integrating cells 712. More specifically, the pre-object filter 704 is constructed such that radiation 714 that is directed toward the central portion of the detector array 708, which comprises rows of photon counting cells 710, is attenuated more (e.g., due to the thicker portion of the pre-object filter 704) than radiation 714 directed toward the edge portions of the detector array 708, which may comprise rows of energy integrating cells 712, for example. It may be appreciated that this thicker portion of the pre-object filter may also extend into and out of the page in the x-direction. For example, the thicker portion may extend into and out of the page a greater degree to accommodate a detector array configuration as illustrated in FIG. 3 than to accommodate a detector array configuration as illustrated in FIG. 6. In this way, radiation 714 directed towards rows and/or portions of rows comprising photon counting cells 710 may be attenuated differently than radiation directed towards rows and/or portions of rows comprising energy integrating cells 712, for example (e.g., to reduce a likelihood of pulse pileup due to a high flux rate often associated with CT systems and other systems configured to image a patient utilizing radiation energy).

It may be appreciated that the thickness of the pre-object filter 704 may also be varied in the x and/or z directions as a function of the placement of the photon counting cells 710 and/or the placement of the photon counting cells 712. For example, the pre-object filter 704 may be configured to attenuate radiation 714 directed to columns and/or portions of columns comprising photon counting cells 710 differently than radiation 714 directed toward columns and/or portions of columns comprising energy integrating cells 712.

Figure 8:
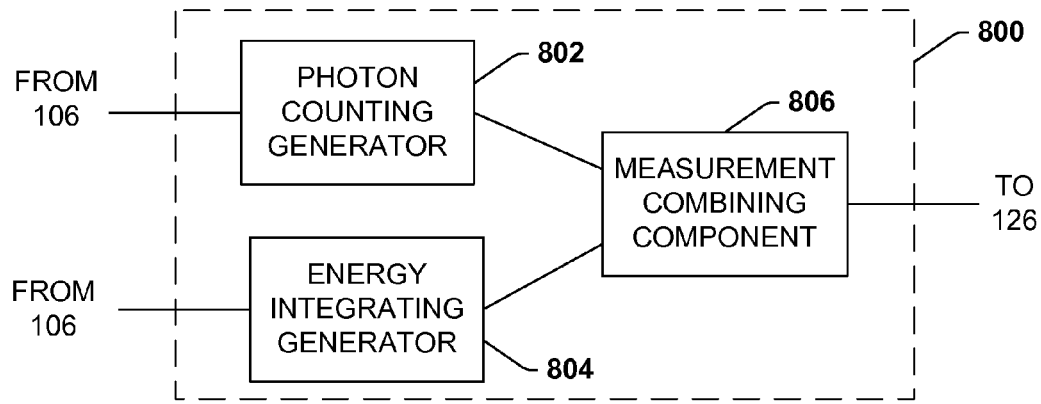
FIG. 8 illustrates an example image generator.

FIG. 8 illustrates an example image generator 800 (e.g., 124 in FIG. 1) configured to generate one or more images of an object under examination and/or that underwent an examination via radiation. The example image generator 800 comprises a photon counting generator 802 configured to generate an image from at least some photon counting measurements yielded from photon counting cells of a detector array (e.g., 106 in FIG. 1) and an energy integrating generator 804 configured to generate an image from at least some energy integrating measurements yielded from energy integrating cells of the detector array using suitable image generation techniques (e.g., backprojection techniques, iterative reconstruction techniques, tomosynthesis techniques, etc.). In this way, at least two images may be generated. A first image, generated by the photon counting generator 802, may be indicative of attenuation as measured by the photon counting cells and a second image, generated by the energy integrating generator 804, may be indicative of attenuation as measured by the photon counting cells.

In one embodiment, the image generator 800 further comprises a measurement combining component 806 configured to combine measurement data yielded from the photon counting cells (e.g., which may be represented by the first image) with measurement data yielded from the energy integrating cells (e.g., which may be represented by the second image). In one embodiment, a combined image may be generated by combining the photon counting measurement data with the energy integrating measurement data. Such an image may be indicative of the measurement data yielded from the photon counting cells and indicative of measurement data yielded from the energy integrating cells.

In one embodiment, the measurement combining component 806 may be further configured to at least one of correct pulse pileup represented in the measurement data yielded from the photon counting cells using the measurement data yielded from the energy integrating cells and/or to separate the measurement data yielded from the energy integrating cells into different energy bins, such as a low energy bin and a high energy bin, for example, (e.g., for wavelength discrimination) using measurement data yielded from the photon counting cells. By way of example, at high flux rates, radiation may impinge the photon counting cells at a rate which exceeds a rate at which the photon counting cells can return to a baseline state after a detection event. As such, a single pulse may be indicative of more than one detection event (e.g., more than one photon strike), leading to the photon counting cell miscounting the number of photons that have impinged upon the photon counting cell. Such an event may be referred to as pulse pileup and may result in fewer photons being counted than actually impinged upon the photon counting cell. In one embodiment, to correct for pulse pileup, the measurement combining component 806 may utilize the measurement data yielded from the energy integrating cells (e.g., where pulse pileup does not occur due to the energy integrating cells integrating charge as opposed to counting respective detection events) to correct pulse pileup in the measurement data yielded from one or more photon counting cells (e.g., using interpolation, extrapolation, or other correction techniques).

As other example, photon counting cells, which measure respective detection events, are typically configured to distinguish energy wavelengths of detected radiation. As an example, photon counting cells (e.g., or measurement electronics coupled to the photon counting cells) may be configured to group detection events by energy level. Detection events representative of detected photons having a first energy spectrum (e.g., a low energy spectrum) may be grouped into a first (e.g., low) energy bin and detection events representative of detected photons having a second energy spectrum (e.g., a higher energy spectrum) may be grouped into a second (e.g., high) energy bin. Typically, energy integrating cells are unable to discriminate energy wavelengths of detected photons. As such, in one embodiment, the measurement combining component 806 may be configured to utilize the measurement data yielded from the photon counting cells (e.g., which can be separated according to wavelength) to separate measurement data yielded from the energy integrating cells into a first energy bin (e.g., indicative of low energy photon events) and a second energy bin (e.g., indicative of higher energy photon events) (e.g., using interpolation, extrapolation, or other separation techniques).

It may be appreciated that although the example measurement combining component 806 is illustrated as being comprised within the image generator 800, in another embodiment the measurement combining component 806 may be located apart from the image generator 800. Moreover, the measurement combining component 806 may be configured to perform the combining, correcting, and/or separating in projection space (e.g., as opposed to in image space as described herein).

The output of the image generator (e.g., transmitted to the terminal 126 in FIG. 1) may be the first image representative of the measurement data yielded from the photon counting cells, the second image representative of the measurement data yielded from the energy integrating cells, and/or the combined image. Moreover, it may be appreciated that in one embodiment, where multiple images are output, the image generator 800 may be configured to correlate the images such that features illustrated in one image are correlated with features illustrated in other image (e.g., so that if one image is manipulated by a user, the other image(s) may be automatically manipulated likewise). Further, the image generator 800 may be responsive to user input which instructs the image generator 800 to output the first image, the second image, and/or the combined image. The measurement combining component 806 may be responsive to user input which instructs the measurement combining component 806 to correct for pulse pileup and/or whether to create a dual-energy image (e.g., by separating measurement data yielded from the energy integrating cells), for example.

It may be appreciated that the foregoing image generator 800 provides merely one example configuration of an image generator and is not intended to limit the scope of the application, including the scope of the claims. By way of example, in another embodiment, the image generator may comprise a single component configured to receive the measurement data yielded from the photon counting cells and the measurement data yielded from the energy integrating cells and to generate an image therefrom.

Figure 9:
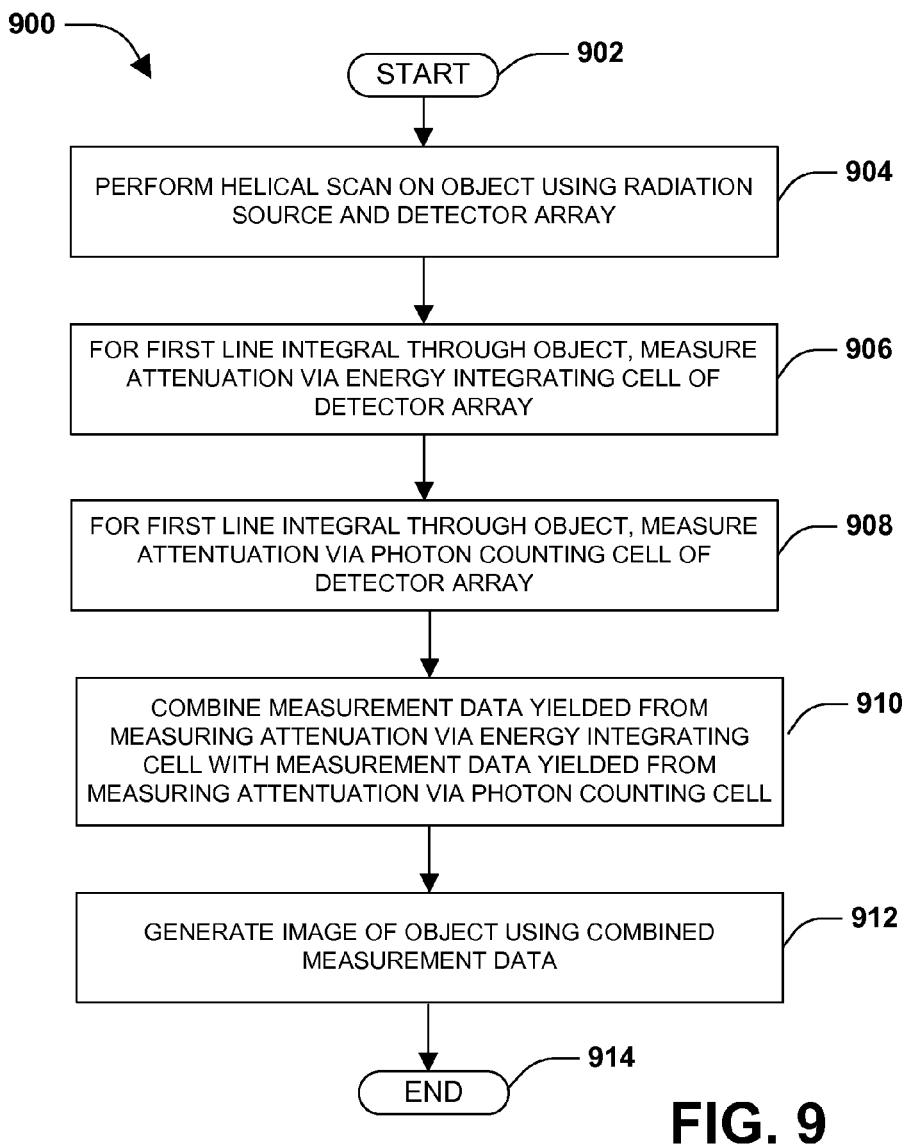
FIG. 9 is an example flow diagram illustrating an example method for imaging an object.

FIG. 9 illustrates an example method 900 for examining and/or imaging an object. The example method 900 begins at 902 and a helical scan is performed on the object using a radiation source and a detector array. As described with respect to FIG. 2, a helical scan may be achieved by varying the position and/or orientation of the object relative to the radiation source and/or detector array (e.g., or relative to a rotating gantry to which the radiation source and detector array are affixed). For example, in one embodiment, the radiation source and/or the detector array may be configured to rotate, in an x,y plane about the object while the object is translated in a z-direction (e.g., such as illustrated in FIG. 2). In another embodiment, the object may be substantially stationary or translated and the radiation source and/or detector array may be configured for both rotation and translation about the object to perform a helical scan. In still other embodiment, the object may be configured for rotation while the radiation source and/or detector array are translated relative to the object. In yet another embodiment, the radiation source and/or detector array may be substantially stationary while the object rotates and is translated relative to the radiation source and/or detector array. Thus, it may be appreciated that there are numerous techniques for scanning an object helically by varying the position/orientation of the radiation source and/or detector array relative to the object, for example.

Attenuation of a first line integral through the object is measured via an energy integrating cell at 906 and via a photon counting cell at 908 in the example method 900. That is, during the helical scan, an amount of radiation following the path of a line integral (e.g., an imaginary line through the object) is measured via a photon counting cell and an energy integrating cell to determine an amount of attenuation caused by sub-objects in the path of the line integral.

It may be appreciated that line-integral measurement inconsistencies between charge-integrating cells and photon-counting cells may be reduced or eliminated by use of dynamic focal-spot wobbling or deflection (e.g., along the z-axis and/or x-axis). Such dynamic deflection allowing, with proper consideration of system geometry and acquisition pitch, to reduce or eliminate the geometric inconsistencies between measurements.

Typically, the measurement of attenuation of the line integral by the energy integrating cell and the measurement of attenuation of the line integral by the photon counting cell are not performed concurrently (e.g., because merely one cell may measure a line integral at a time unless the photon counting cell and energy integrating cell are overlapping). As such, the attenuation of the line integral may be measured via the energy integrating cell during a first rotation segment of the helical scan and may be measured via the photon counting cell during a second rotation segment of the helical scan. For example, the energy integrating cell may measure the attenuation of the line integral during a first portion of a first rotation and the photon counting cell may measure the attenuation of the line integral during a second portion of the first rotation, where the first and second portions of the first rotation are different (e.g., 180 degrees apart). As another example, the energy integrating cell may measure the attenuation of the line integral during a first rotation of the helical scan and the photon counting cell may measure the attenuation of the line integral during a second rotation of the helical scan, where the first rotation is a different (full) rotation than the second rotation. Thus, the first and second rotation segments may be part of a single rotation or the first rotation segment may be a portion of a first rotation and the second rotation segment may be a portion of a second rotation.

It may be appreciated that although reference is made to the energy integrating cell measuring attenuation during a first rotation segment and the photon counting cell measuring attenuating during a second rotation segment, the order of the measurements may be immaterial. Thus, attenuation of the first line integral may be measured by the photon counting cell at 908 prior to the attenuation of the first line integral being measured by the energy integrating cell at 906. As such, the terms first and second are merely intended to assist in distinguishing features and are not intended to imply a temporal order (e.g., unless otherwise specified).

As previously described, to measure attenuation of the first line integral via a photon counting cell and via an energy integrating cell, the detector array may comprise photon counting cells and energy integrating cells. In one embodiment, the arrangement of such cells within the detector array may be utilized to set a pitch for the helical scan (e.g., a speed of translation of the object, radiation source, and/or detector array) and/or to set a rotational speed (.e.g., of the object, radiation source, and/or detector array). That is, the pitch and/or rotational speed may be set based upon the arrangement of the detector cells such that the first line integral can be measured by both a photon counting cell and an energy integrating cell.

In one embodiment, the acts described at 906 and 908 may be repeated for a plurality of line integrals such that, for respective line integrals of the plurality of line integrals, attenuation is measured via at least one energy integrating cell and at least one photon counting cell during a helical scan of the object. In this way, at least two substantially complete views (e.g., from which 3D images may be derived) of an object may be acquired, one from measurements yielded from the photon counting cells and one from measurements yielded from the energy integrating cells.

It may be appreciated that although reference is made to merely measuring attenuation of the first line integral via one energy integrating cell and one photon counting cell, the attenuation of the first line integral may be measured by more than one photon counting cell and/or more than one energy integrating cell.

Moreover, as described with respect to FIG. 7, in one embodiment, it may be desired to attenuate at least a portion of the radiation directed toward the object by a pre-object filter (e.g., to reduce an amount of radiation that could potentially impinge a portion of the detector array and/or to reduce dose to the object). For example, in one embodiment, radiation directed toward at least some photon counting cells may be attenuated differently than radiation directed toward energy integrating cells. In this way, radiation directed toward the at least some photon counting cells (e.g., which function better at lower flux rates due to photon saturation (e.g., which leads to pulse pileup) at higher flux rates) may be attenuated more, for example, than radiation directed toward the at least some energy integrating cells, for example.

At 910 in the example method 900, measurement data yielded from measuring attenuation via the energy integrating cell and measurement data yielded from measuring attenuation via the photon counting cell may be combined, and an image of the object may be generated using the combined measurement data at 912.

As previously described, such measurement data may be combined in projection space or in image space. For example, in one embodiment, the measurement data may be combined in projection space and the combined data may be transmitted to an image generator to generate an image from the combined data. In another embodiment, the measurement data yielded from the photon counting cell (e.g., along with measurement data yielded from other photon counting cells) may be utilized to generate a first image and the measurement data yielded from the energy integrating cell (e.g., along with measurement data yielded from other energy integrating cells) may be utilized to generate a second image. The first and second images may then be combined to form a combined image, for example.

It may be appreciated that, in one embodiment, as part of combining measurement data and/or as a separate feature, a portion of the measurement data yielded from the photon counting cell may be modified based upon the measurement data yielded from the energy integrating cell and/or vice-versa. For example, measurement data yielded from measuring attenuation via the energy integrating cell may be separated into high and low energy bins (e.g., for energy discrimination) using the measurement data yielded from measuring attenuation via the photon counting cell. That is, measurement data from which energy discrimination may be derived (e.g., the measurement data yielded from the photon counting cell) may be utilized to derive energy discrimination information in the measurement data yielded from the energy integrating cell (e.g., which typically contains no energy discrimination information).

As another example, measurement data yielded from the energy integrating cell may be utilized to correct for pulse pileup represented in measurement data yielded from the photon counting cell (e.g., which may have been unable to count each photon impinging thereon due to photon saturation). As such, measurement data from an energy integrating cell (e.g., where pulse pileup typically does not occur due to the differences in how a change integrating cell measures energy relative to how a photon counting cell measures energy) may be utilized to correct pulse pileup in measurement data yielded from a photon counting cell.

The example method 900 ends at 914.

Figure 10:
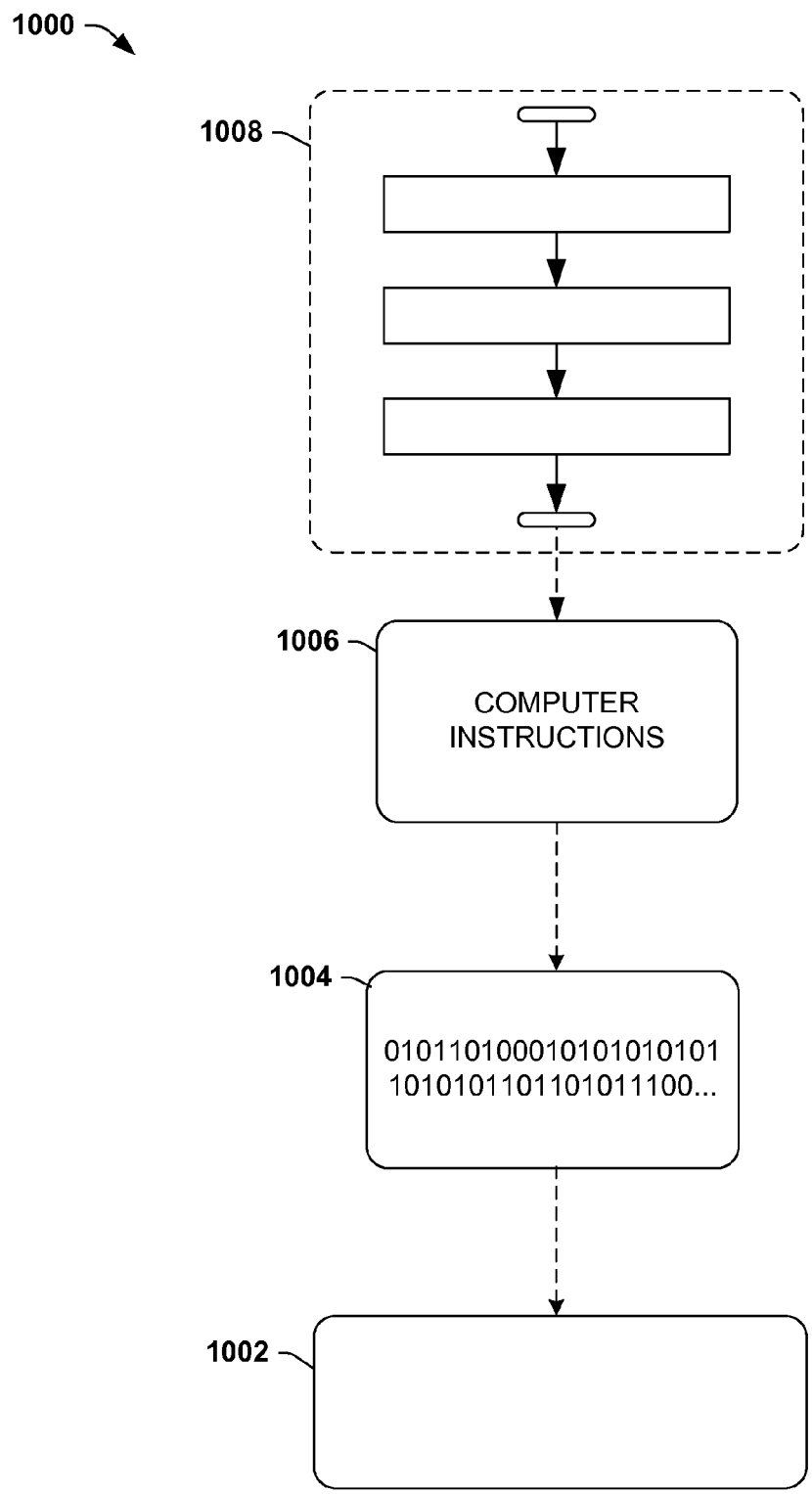
FIG. 10 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 10, wherein the implementation 1000 comprises a computer-readable medium 1002 (e.g., a flash drive, CD-R, DVD-R, application-specific integrated circuit (ASIC), field-programmable gate array (FPGA), a platter of a hard disk drive, etc.), on which is encoded computer-readable data 1004. This computer-readable data 1004 in turn comprises a set of computer instructions 1006 configured to operate according to one or more of the principles set forth herein. In one such embodiment 1000, the processor-executable instructions 1006 may be configured to perform a method 1008, such as at least some of the example method 900 of FIG. 9, for example. In another such embodiment, the processor-executable instructions 1006 may be configured to implement a system, such as at least some of the exemplary systems 100 and/or 800 of FIGS. 1 and 8, respectively, for example. Many such computer-readable media may be devised by those of ordinary skill in the art that are configured to operate in accordance with one or more of the techniques presented herein.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally to be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application.

What is claimed is:

1. An imaging apparatus, comprising:
an examination region configured to selectively receive an object under examination;
a radiation source; and
a detector array configured to detect radiation emitted from the radiation source that has traversed the object, the detector array comprising energy integrating cells and photon counting cells.

2. The apparatus of claim 1, wherein the imaging apparatus is a computed tomography system and the imaging apparatus comprises:
a rotating gantry configured to rotate the radiation source and the detector array about the examination region while maintaining a relative position of the radiation source and the detector array.

3. The apparatus of claim 2, wherein the detector array comprises a plurality of rows of cells extending in an x-direction, a first row of cells comprising the photon counting cells and a second row of cells comprising the energy integrating cells.

4. The apparatus of claim 3, wherein the detector array comprises a central portion and edge portions, the first row of cells comprised in the central portion and the second row of cells comprised in an edge portion.

5. The apparatus of claim 1, wherein the detector array has an arcuate detection surface.

6. The apparatus of claim 1, wherein an energy integrating cell has a first detection surface area and a photon counting cell has a second detection surface area, the first detection surface area different than the second detection surface area.

7. The apparatus of claim 6, wherein the second detection surface area is less than the first detection surface area.

8. The apparatus of claim 1, wherein the radiation source comprises an ionizing radiation source.

9. The apparatus of claim 1, comprising:
a pre-object filter configured to attenuate a portion of the radiation prior to interaction with the object, the pre-object filter configured to attenuate more radiation directed toward at least some of the photon counting cells than directed toward at least some of the energy integrating cells.

10. The apparatus of claim 1, comprising:
a measurement combining component configured to combine measurement data yielded from the photon counting cells with measurement data yielded from the energy integrating cells.

11. The apparatus of claim 10, the measurement combining component configured to at least one of:
correct pulse pileup represented in the measurement data yielded from the photon counting cells using the measurement data yielded from the energy integrating cells; or
separate the measurement data yielded from the energy integrating cells into a first energy bin and a second energy bin using the measurement data yielded from the photon counting cells.

12. A method for imaging an object, comprising:
performing a helical scan on an object using a radiation source and a detector array; and
for a first line integral through the object,
measuring attenuation of the first line integral via an energy integrating cell of the detector array; and
measuring the attenuation of the first line integral via a photon counting cell of the detector array.

13. The method of claim 12, wherein the attenuation of the first line integral is measured via the energy integrating cell during a first rotation segment of the helical scan and the attenuation of the first line integral is measured via the photon counting cell during a second rotation segment of the helical scan, the first rotation segment different than the second rotation segment.

14. The method of claim 12, comprising setting a pitch for the helical scan based upon a relative position of the energy integrating cell and the photon counting cell.

15. The method of claim 12, comprising:
combining measurement data yielded from measuring the attenuation via the energy integrating cell with measurement data yielded from measuring the attenuation via the photon counting cell to yield combined measurement data; and
generating an image of the object using the combined measurement data.

16. The method of claim 12, comprising:
separating measurement data yielded from measuring attenuation via the energy integrating cell into a first energy bin and a second energy bin using measurement data yielded from measuring attenuation via the photon counting cell.

17. The method of claim 12, comprising correcting for pulse pileup represented in measurement data yielded from measuring attenuation via the photon counting cell using measurement data yielded from measuring attenuation via the energy integrating cell.

18. The method of claim 12, comprising attenuating, by a pre-object filter, at least a portion of radiation emitted during the helical scan, radiation directed toward the photon counting cell attenuated differently than radiation directed toward the energy integrating cell.

19. A computer-tomography apparatus for medical imaging, comprising:
an examination region configured to selectively receive an object under examination;
a radiation source;
a detector array configured to detect radiation emitted from the radiation source that has traversed the object, the detector array having an arcuate detection surface, a first portion of the arcuate detection surface comprising photon counting cells and a second portion of the arcuate detection surface comprising energy integrating cells; and
a rotating gantry configured to rotate the radiation source and the detector array about the examination region during a helical examination of the object.

20. The apparatus of claim 19, wherein the photon counting cells are configured for direct conversion of radiation impinging thereon into electrical energy and the energy integrating cells are configured for indirect conversion of radiation imaging thereon into electrical energy.

* * * * *